US00PP31582P2

(12) United States Plant Patent
Olesen et al.

(10) Patent No.: US PP31,582 P2
(45) Date of Patent: Mar. 24, 2020

(54) ***CLEMATIS* PLANT NAMED 'EVIPO102'**

(50) Latin Name: *Clematis viticella*
Varietal Denomination: Evipo102

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,897

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 6/72
See application file for complete search history.

(56) References Cited

PUBLICATIONS

Poulsen Roser A/S (http://www.poulsenroser.com/assortment/clematis-collections/boulevard/pantheon.aspx, retrieved from internet on Jun. 27, 2019).*

* cited by examiner

*Primary Examiner* — Keith O. Robinson

(57) ABSTRACT

A new *Clematis* plant with a compact growth habit, profuse, Red-Purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo102'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo102' originated as a single seedling from the stated cross.

The new *Clematis* plant may be distinguished from its female seed parent and male pollen parent by the following characteristics. The female seed parent has Red-Purple Group 59D colored tepals while the new variety has Red-Purple 60B and 61B colored tepals. The male seed parent has a growth height over 150 cm, while the new variety is more compact, growing to about 100 cm in height.

The objective of the hybridization of this *Clematis* plant was to create a new and distinct variety for nursery culture with unique qualities such as:

1. Uniform and abundant Red-Purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo102' was selected by Mogens N. Olesen and Raymond J. Evison in their *Clematis* development program in the Channel Islands, United Kingdom in 2006. Asexual reproduction of 'Evipo102' by means of vegetative stem cuttings and traditional layering was first performed by Mogens N. Olesen and Raymond J. Evison in the nursery during the summer of 2006. This initial and subsequent asexual propagations have demonstrated that the characteristics of 'Evipo102' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo102'.

Specifically illustrated in FIG. 1 of the drawings are an open flower, detached tepals, and reproductive flower parts.

DETAILED DESCRIPTION OF THE VARIETY

Figure 1:
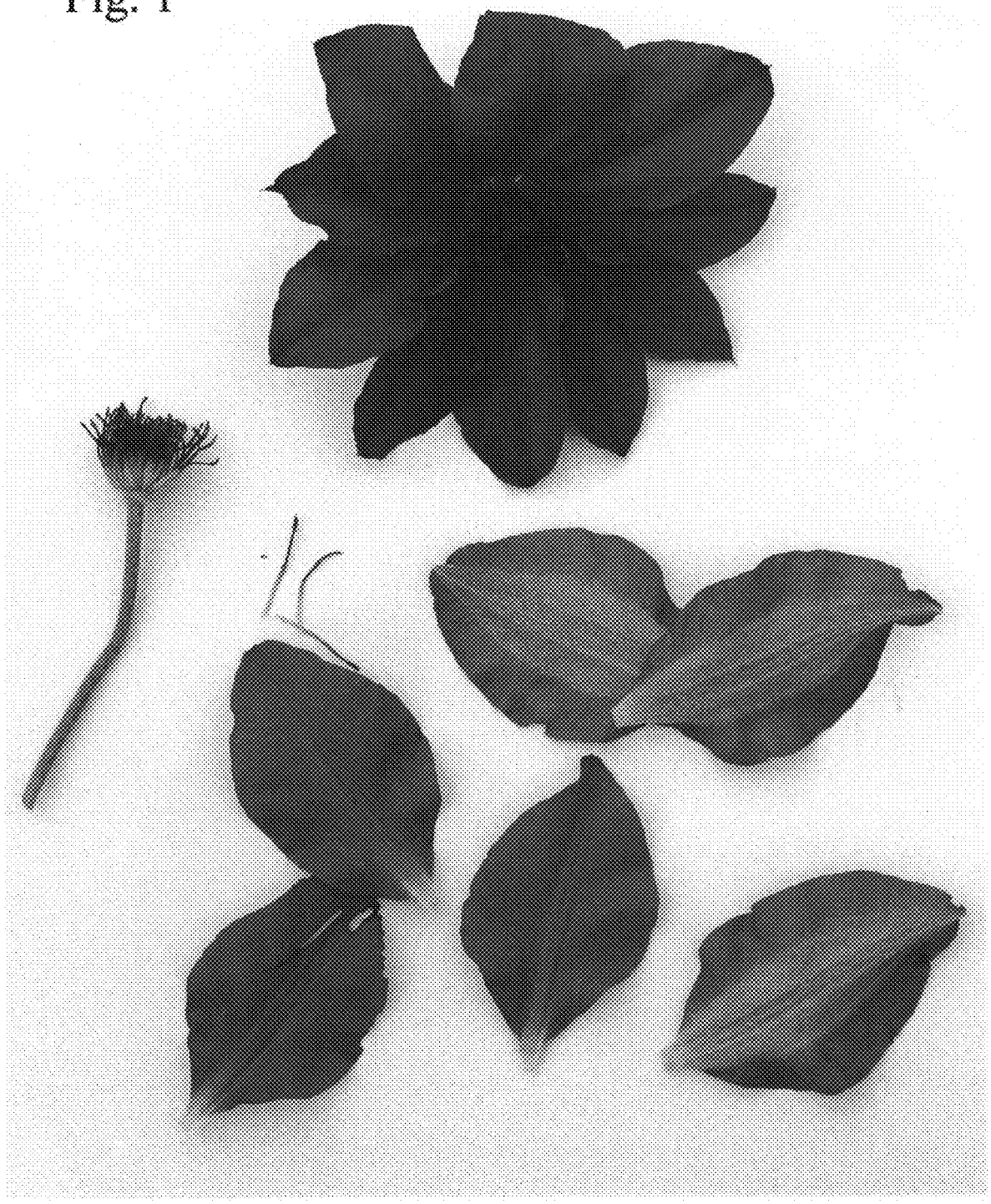
Figure 2:
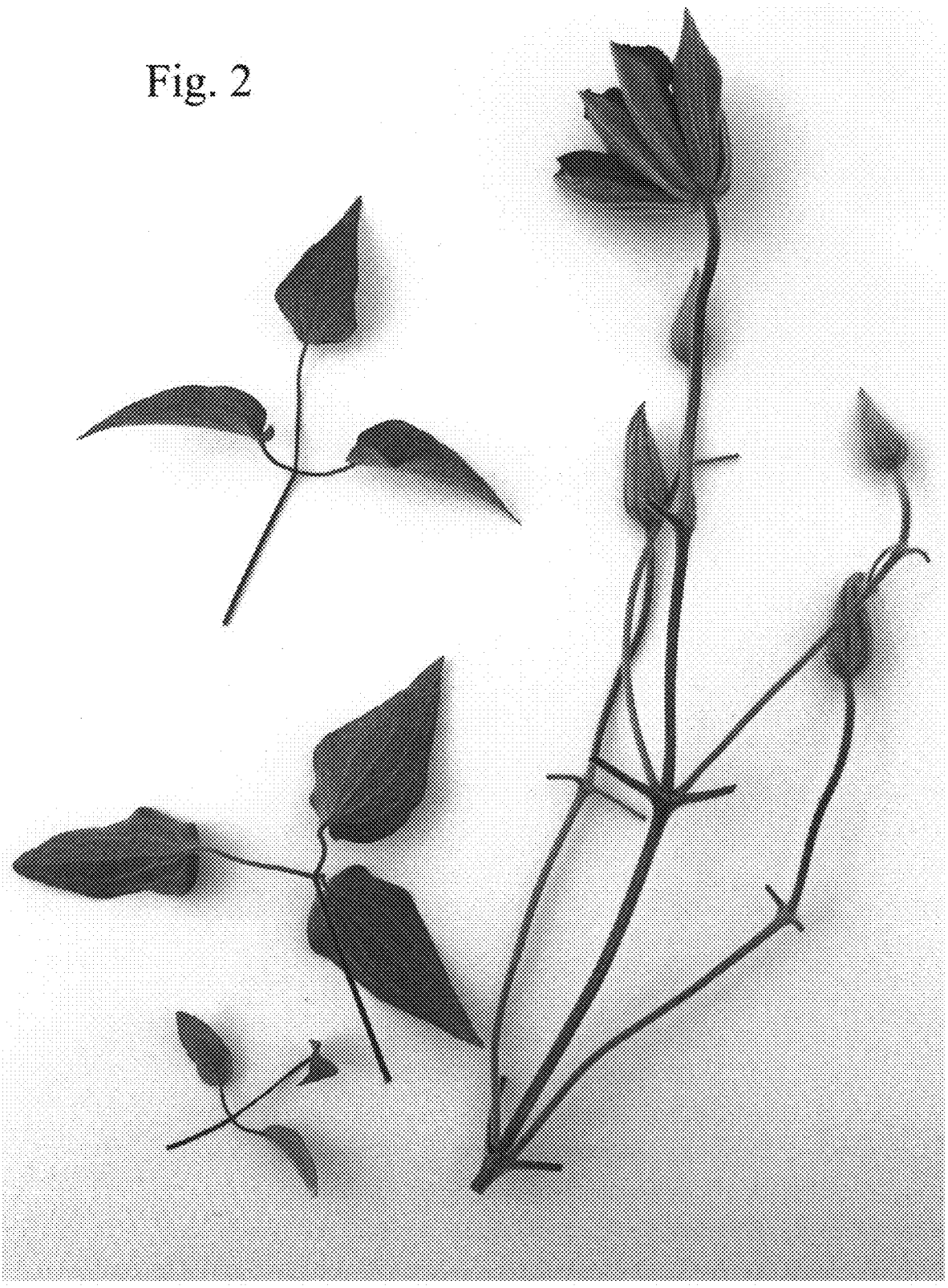
FIG. 2 shows leaves, stems, and a cluster of flower buds attached to the stem. Illustrated plants are 2 years of age.

The following is a detailed description of 'Evipo102', as observed in its growth throughout the flowering period in Marion County Oreg. Observed plants were cultivated for a period of 24 months in an open field. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo056' described and illustrated in U.S. Plant Pat. No. 27,279 are compared to 'Evipo102' in Chart 1.

CHART 1

| | 'Evipo102' | 'Evipo056' |
|---|---|---|
| Flower diameter | 120 mm | 80-100 mm |
| Tepal upper surface after opening | Red-Purple Group 60B with intonations of Red-Purple Group 61B | Purple-Violet Group 82C with a central stripe Purple-Violet Group 81A |
| Tepal count | 10 | 6 |

FLOWER AND FLOWER BUD

Blooming habit: Continuous. The natural flowering period is generally from April to September. Flower buds develop on current year's growth only.

Flower bud:

*Size.*—Normally 35 mm in length. Bud diameter is 15 mm.

*Bud form.*—Long campanulate, broad based.

*Bud color.*—Yellow-Green Group 145 C with intonations of Greyed-Orange Group 174B.

*Texture.*—Very pubescent.

Pedicel:

*Surface Texture.*—Smooth.

*Length.*—On average 35 to 85 mm in length with 3.5 mm diameter.

*Color.*—Yellow-Green Group 144B with intonations of Greyed-Purple Group 183B.

*Strength.*—Moderate.

Receptacle:

*Surface Texture.*—Pubescent.

*Shape.*—Broad funnel.

*Size.*—2 mm (h)×3 mm (w).

*Color.*—Yellow-Green Group 144B.

Flower arrangement:

*Location on vine.*—New and old growth. Flowering occurs about 20 cm from the base of the plant.

*Borne.*—Arranged solitary. Single flower buds develop, from terminal and axillary buds along the branch.

Flower bloom:

*Size.*—On average, flowers are 120 mm in diameter and 30 mm in depth.

*Profile.*—Open flowers are flat.

*Fragrance.*—None.

*Lasting quality.*—Flowers normally remain up to 10 days on the plant.

*Attitude.*—Outwards.

Tepals:

*Tepal color.*—Upon opening, the upper surface is Red-Purple Group 60B with intonations of Red-Purple Group 61B. There is a spot at the upper portion of the tepal base of Green-White Group 157A. The lower surface is Red-Purple Group 70A at tepal margins, and a central bar of Purple Group 75A. Additional colorations in the central bar are Yellow-Green Group 147D.

*Quantity.*—Normally 10 tepals.

*Size.*—75 mm in length by 40 mm wide.

*Shape.*—Individual tepal shape is elliptic. Tepal apex and base are acute.

*Apex recurvature.*—None.

*Tepal cross section.*—Flat.

*Margins.*—Entire. Very weak undulations of margin observed.

*Persistence.*—Tepals drop off cleanly.

*Arrangement.*—Overlapping.

Reproductive organs:

*Pollen.*—None observed.

*Anthers.*—Size: 8 mm in length. Color: Purple Group N77A. Quantity: On average, 45.

*Filaments.*—Color: Red-Purple Group 69C at the base. The upper portion is Red-Purple Group 62A. Length: 15 mm.

*Pistils.*—Quantity: On average, 20.

*Stigmas.*—Inferior in location relative to the length of the filaments and the height of the anthers.

*Styles.*—Color: Green-White Group 157C. Length: 15 mm.

*Seed head characteristics.*—Seed not observed to date.

PLANT

Plant form: Climbing.

Plant growth: Moderately compact.

Size: Seasons growth attains 100 cm in height. Average spread is 50 cm.

Stems:

*Color.*—Juvenile stems are Yellow-Green Group 144B. Mature stems are Yellow-Green Group 144B with intonations of Greyed-Red Group 178C.

*Internodes.*—On average, 105 mm between nodes.

*Length.*—Normally 20 cm from the base of the plant to the flowering portion of the stem.

*Diameter.*—About 4 mm.

*Texture.*—Mature stems are ribbed, and pubescent.

Plant foliage:

*Leaf characteristics.*—Deciduous.

*Arrangement.*—Ternate.

*Leaf size.*—Compound leaves are about 140 mm (1)× 145 mm (w). Leaflets are about 55 mm (1)× 29 mm (w).

*Abundance.*—On average 2 leaves per 10 cm of stem.

*Leaf color.*—Juvenile upper Yellow-Green Group 144B. Juvenile lower Yellow-Green Group 144B with margins Greyed-Orange Group 166A. Mature upper Yellow-Green Group 146A. Mature lower Yellow-Green Group 146B.

*Stipules.*—Absent.

*Petioles.*—Size: Normally 60 mm in length by 2 mm diameter. Texture: Smooth. Color: Yellow-Green Group 144B, with intonations of Greyed-Orange Group 166A.

*Petioloule.*—Size: About 35 mm in length by 1.5 mm diameter. Texture: Smooth. Color: Yellow-Green Group 144B, with intonations of Greyed-Orange Group 166A.

*Leaflet shape.*—Ovate. The base is rounded, apex acute.

*Margin.*—Entire.

*Surface.*—The upper side is smooth, the lower side is smooth.

*Thickness.*—Moderate.

*Glossiness.*—Moderately glossy.

Disease resistance: Subject to any disease that normally attacks the species. However the variety is more tolerant to *Clematis* wilt, *Ascochyta clematidina,* than some *Clematis* known to the inventors.

Cold hardiness: The variety is tolerant to USDA Hardiness Zone 6.

Heat tolerance: The variety has been found to be suitable for climate conditions found in The American Horticulture Society heat zone 7.

We claim:

1. A new and distinct variety of *Clematis* plant named 'Evipo102', substantially as described and illustrated , due to its abundant Red-Purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *